United States Patent
Liu et al.

(10) Patent No.: US 7,118,753 B2
(45) Date of Patent: Oct. 10, 2006

(54) ENHANCING CELL-BASED IMMUNOTHERAPY

(75) Inventors: Shih-Jen Liu, Taipei (TW); Wei-Yu Lo, Taipei (TW)

(73) Assignee: Anawrahta Biotech Co., Ltd., Taipei-Shien (TW)

( * ) Notice: Subject to any disclaimer, the term of this patent is extended or adjusted under 35 U.S.C. 154(b) by 332 days.

(21) Appl. No.: 10/072,185

(22) Filed: Feb. 8, 2002

(65) Prior Publication Data

US 2003/0152555 A1    Aug. 14, 2003

(51) Int. Cl.
*A61K 39/385* (2006.01)
*A61K 39/00* (2006.01)
*A61K 38/28* (2006.01)

(52) U.S. Cl. .................. 424/193.1; 514/4; 424/185.1

(58) Field of Classification Search ............ 424/185.1, 424/192.1, 93.71, 93.7
See application file for complete search history.

(56) References Cited

U.S. PATENT DOCUMENTS 5,837,251 A * 11/1998 Srivastava ............... 424/193.1
5,891,653 A *  4/1999 Attfield .................... 435/7.21
5,985,270 A * 11/1999 Srivastava ............... 424/93.71

OTHER PUBLICATIONS

Tong et al., "Combined Intratumoral injection of Bone Marrow-derived Dendritic Cells and Systemic Chemotherapy to Treat Pre-existing Murine Tumors", Cancer Research, 2001, 61:7530-7535.*
Suzue et al., "Adjuvant-free hsp70 fusion protein system elicits humoral and cellular immune responses to HIV-1 p. 24 ", Journal of Immunology, 1996, 156:873-879.*
Janeway et al., "Immunobiology, Third Edition" (1997) Garland Publishing Inc., pp. G:2 and G:11.*
Alberts et al., "Molecular Biology of the Cell, Third Edition", (1994) Garland Publishing Inc., pp. 308-331.*
Rubartelli et al., "The Selective Engulfment of Apoptotic Bodies by Dendritic Cells is Mediated by the $\alpha v \beta 3$ Integrin and Requires Intracellular and Extracellular Calcium", Eur. J. Immunol. 27:1893-1900, 1997.
Lutz et al., "An Advanced Culture Method for Generating Large Quantities of Highly Pure Dendritic Cells from Mouse Bone Marrow", Journal of Immunological Methods 223:77-92, 1999.

* cited by examiner

*Primary Examiner*—Misook Yu
*Assistant Examiner*—Judy Lille Tidwell
(74) *Attorney, Agent, or Firm*—Fish & Richardson P.C.

(57) ABSTRACT

An immunogenic composition containing antigen-presenting cells and a heat shock protein or a heat shock fusion protein. Also disclosed is a method of using such a composition for enhancing cell-based immunotherapy, especially cancer immunotherapy. The method includes administering the composition to a target site.

12 Claims, No Drawings

SEQUENCE LISTING

<160> NUMBER OF SEQ ID NOS: 8

<210> SEQ ID NO 1
<211> LENGTH: 26
<212> TYPE: DNA
<213> ORGANISM: Artificial Sequence
<220> FEATURE:
<223> OTHER INFORMATION: Primer

<400> SEQUENCE: 1
cgcggatcca tggccaaagc cgcggc                                          26

<210> SEQ ID NO 2
<211> LENGTH: 29
<212> TYPE: DNA
<213> ORGANISM: Artificial Sequence
<220> FEATURE:
<223> OTHER INFORMATION: Primer

<400> SEQUENCE: 2
cgcggatccc taatctacct cctcaatgg                                       29

<210> SEQ ID NO 3
<211> LENGTH: 31
<212> TYPE: DNA
<213> ORGANISM: Artificial Sequence
<220> FEATURE:
<223> OTHER INFORMATION: Primer

<400> SEQUENCE: 3
gggaattcgc gatgccaacg gcatcctgaa c                                    31

<210> SEQ ID NO 4
<211> LENGTH: 30
<212> TYPE: DNA
<213> ORGANISM: Artificial Sequence
<220> FEATURE:
<223> OTHER INFORMATION: Primer

<400> SEQUENCE: 4
ggaaatttct aatctacctc ctcaatggtg                                      30

<210> SEQ ID NO 5
<211> LENGTH: 30
<212> TYPE: DNA
<213> ORGANISM: Artificial Sequence
<220> FEATURE:
<223> OTHER INFORMATION: Primer

<400> SEQUENCE: 5
gcggatccac actgcataga aatgaatatg                                      30

<210> SEQ ID NO 6
<211> LENGTH: 28
<212> TYPE: DNA
<213> ORGANISM: Artificial Sequence
<220> FEATURE:
<223> OTHER INFORMATION: Primer

<400> SEQUENCE: 6
gcggatccaa ctcccaaagc agcacgag                                        28

<210> SEQ ID NO 7
<211> LENGTH: 20

```
<212> TYPE: DNA
<213> ORGANISM: Artificial Sequence
<220> FEATURE:
<223> OTHER INFORMATION: Primer

<400> SEQUENCE: 7
attgtgggag gctgggagtg                                              20

<210> SEQ ID NO 8
<211> LENGTH: 19
<212> TYPE: DNA
<213> ORGANISM: Artificial Sequence
<220> FEATURE:
<223> OTHER INFORMATION: Primer

<400> SEQUENCE: 8
ggggttggcc acgatggtg                                               19
```

ENHANCING CELL-BASED IMMUNOTHERAPY

BACKGROUND OF THE INVENTION

Cellular immunity is carried out by T cells that recognize antigens on the surface of antigen-presenting cells. The most potent antigen-presenting cells are the highly specialized dendritic cells. Other antigen-presenting cells include macrophages and B cells. Although macrophages and B cells can present antigens efficiently to memory T cells, they are less efficient than dendritic cells in initiating immune responses mediated by naive T cells.

Induction of T cell responses is known to be critical for anti-tumor effects. Recent development of techniques in generating dendritic cells in large numbers in vitro from peripheral blood monocytes or hematopoietic progenitors has led to new approaches in cancer immunotherapy.

SUMMARY OF THE INVENTION

The present invention provides an immunogenic composition and a method of using such a composition for enhancing cell-based immunotherapy, especially cancer immunotherapy. The invention is based on the finding that the combination of dendritic cells and/or other antigen-presenting cells with heat shock proteins or heat shock fusion proteins can inhibit the growth of tumor and induce long-term cellular immunity.

The immunogenic composition of this invention contains antigen-presenting cells (e.g., dendritic cells), a heat shock protein or a heat shock fusion protein, and a pharmaceutically acceptable carrier (e.g., a buffer). It can further contain a cytotoxic compound (i.e., a compound capable of inducing cell death). The antigen-presenting cells can be purified, e.g., from bone marrow. The heat shock protein or heat shock fusion protein can be provided as purified proteins.

The heat shock protein can be, for example, Hsp70, Hsp96, Hsp65 or Hsp27. A combination of different heat shock proteins can be used in the composition.

The heat shock fusion protein can contain a tumor associated antigen (TAA), a polypeptide encoded by an oncogene or a functional fragment thereof, or a tumor suppressor protein or a functional fragment thereof. Examples of TAAs include alfa-fetal protein (AFP), prostate specific antigen (PSA), prostate specific membrane antigen (PSCA), prostate alkaline phosphate (PAP), carcinoembryonic antigen (CEA), Muc-1, HER-2/Neu, MAGE-1, human papillomavirus derived proteins E6 and E7, Epstein-Barr virus proteins EBNA1, and LMP1; examples of oncogenes include c-myc, K-ras, and bcr-abl; and examples of tumor suppressor genes include p53, Rb, adenomatous polyposis coli (APC), and p16.

Another immunogenic composition of this invention contains antigen-presenting cells expressing a heat shock protein or a heat shock fusion protein, and a pharmaceutically acceptable carrier.

The compositions of this invention can be administered to a target site (e.g., a tumor site) to kill unwanted cells including tumor cells. Cell death at the target site may have been induced by irradiation or administration of anti-tumor drugs. Alternatively, it can be induced by a cytotoxic compound co-administered with the other members of the above-described compositions.

Another method of this invention includes administering antigen-presenting cells to a target site. Pre-existing cells at the target site have been manipulated (e.g., by gene transfer) to express a heat shock protein or a heat shock fusion protein.

The present invention provides an immunogenic composition and a method for enhancing cell-based immunotherapy, especially cancer immunotherapy. The details of one or more embodiments of the invention are set forth in the accompanying description below. Other advantages, features, and objects of the invention will be apparent from the description, and from the claims.

DETAILED DESCRIPTION OF THE INVENTION

The present invention provides a method and an immunogenic composition for enhancing cell-based immunotherapy, especially for cancer immunotherapy, in which the combination of dendritic cells and/or other antigen-presenting cells with a heat shock protein or a heat shock fusion protein inhibits the growth of tumor and induces long-term cellular immunity.

Theoretically, combination of defined and undefined antigens in dendritic cell immunotherapy may improve the anti-tumor effect. This invention relates to administering dendritic cells and/or other antigen-presenting cells to target sites, especially dead tumor sites, in the presence of HSPs or HSP fusion proteins. Aforementioned heat shock proteins or heat shock fusion proteins may be added to or expressed in antigen-presenting cells or target sites by gene transfer.

Aforementioned cancer include, but is not limited to human sarcomas and carcinomas, e.g., acoustic neuroma, adenocarcinoma, angiosarcoma, astrocytoma, basal cell carcinoma, bile duct carcinoma, bladder carcinoma, breast cancer, chordoma, bronchogenic carcinoma, cervical cancer, chondrosarcoma, choriocarcinoma, colon carcinoma, craniopharyngioma, cystadenocarcinoma, embryonal carcinoma, endotheliosarcoma, ependymoma, epithelial carcinoma, Ewing's tumor, fibrosarcoma, glioma, hemangioblastoma, hepatoma, leiomyosarcoma, leukemia, liposarcoma, lung carcinoma, lymphangiosarcoma, lymphangioendotheliosarcoma, lymphoma, medullary carcinoma, medulloblastoma, melanoma, meningioma, mesothelioma, multiple myeloma, myxosacroma, neuroblastoma, oligodendroglioma, osteogenic sarcoma, ovarian cancer, pancreatic cancer, papillary adenocarcinomas, papillary carcinoma, pinealoma, prostate cancer, renal cell carcinoma, retinoblastoma, rhabdomyosarcoma, sebaceous gland carcinoma, seminoma, small cell lung carcinoma, squamous cell carcinoma, sweat gland carcinoma, synovioma, testicular tumor, Waldenstrom's macroglobulinemia and Wilms' tumor.

The antigen-presenting cells that are administered to target sites can be purified.

The immunogenic composition can be used with a pharmaceutically acceptable carrier.

When dendritic cells are exposed to irradiated tumor cells that have undergone apoptosis or necrosis, they stimulate the immune response. Moreover, anti-tumor drugs like cyclophosphamide, 5-fluoruracil, doxorubicin, Taxol, and cisplatin, or other physical methods which can induce tumor cell death can be combined with injection of dendritic cells and HSPs or HSP fusion proteins into tumor sites. This treatment enhances therapeutic effects of dendritic cell-based therapy and induces long-term anti-tumor immunity.

The fusion partners of HSP can be full or partial sequences of tumor associated antigens (TAAs), oncogenes or tumor suppressor genes. Many TAAs have been identified, including alfa-fetal protein (AFP) in hepatocellular carcinoma; prostate specific antigen (PSA), prostate specific membrane antigen (PSCA), prostate alkaline phosphate (PAP) in prostate cancer; carcinoembryonic antigen (CEA) in colon or lung cancer; Muc-1 in colorectal and lung cancer; HER-2/Neu in breast cancer; MAGE-1 in melanoma; human papillomavirus derived proteins E6 and E7 in cervical cancer; Epstein-Barr virus proteins EBNA1, LMP1 in nasopharyngeal carcinoma (NPC). The oncogenes include c-myc, K-ras, and bcr-abl. The tumor suppressor genes include p53, Rb, adenomatous polyposis coli (APC), and p16.

The heat shock protein used in the following example is Hsp70. Other proteins in this family, e.g., Hsp96, Hsp65, and Hsp27, are expected to have the same effects. They can be used alone or in any combination. The C-terminal region of a HSP protein may be used to generate fusion proteins.

Our strategies are focused on in situ administration of dendritic cells in combination with HSPs or HSP fusion proteins to dead tumor cells to enhance anti-tumor effects. The treatment leads to effective antigen-presenting cell activation and have the potential to cross-prime tumor antigen-specific CTL response. The same strategy can be applied to other antigen-presenting cells (i.e., macrophages and B cells).

The specific examples below are to be construed as merely illustrative, and not limitative of the remainder of the disclosure in any way whatsoever. Without further elaboration, it is believed that one skilled in the art can, based on the description herein, utilize the present invention to its fullest extent. All publications recited herein are hereby incorporated by reference in their entirety.

EXAMPLES

In this example, we illustrated that Hsp70 or Hsp70-C-terminal fused with AFP and PSA in combination with dendritic cells can enhance anti-tumor effects and long-term immunity after irradiation.

1. Materials and Methods 1.1. Cloning of Hsp Gene and Plasmid Construction

Hsp70 gene was amplified from human hepatocellular carcinoma HepG2 cDNA with a gene-specific forward primer: 5'-cgcggatccATGGCCAAAGCCGCGGC-3', and a gene-specific reverse primer: 5'-cgcggatccCTAATCTAC-CTCCTCAATGG-3' (SEQ ID NO:2). The 1.92 kb Hsp DNA fragment was cleaved with BamHI and ligated with a BamHI-cleaved pRSETA vector. After transformation, plasmids were prepared from an overnight culture of transformed $E.$ $coli$ clones, and further analyzed by restriction enzyme digestion and sequencing. The recombinant plasmid containing Hsp70 gene was named as pRSETA/Hsp70.

Hsp C-terminal DNA fragment was amplified from pRSETA/Hsp70 with an HspC'-specific forward primer: 5'-gggaattcGCGATGCCAACGGCATCCTGAAC-3' (SEQ ID NO:3) and an HspC'-specific reverse primer: 5'-ggaaatttCTAATCTACCTCCTCAATGGTG-3' (SEQ ID NO:4). The 0.5 kb HspC' DNA fragment was cleaved with ApoI and ligated with an EcoRI-cleaved pRSET vector. After transformation, plasmids were prepared from an overnight culture of transformed $E.$ $coli$ clones, and further analyzed by restriction enzyme digestion and sequencing. The recombinant plasmid containing Hsp C-terminal DNA fragment was named as pRSET/HspC', which served as a backbone for construction of tumor antigen-HspC' expression plasmids.

1.2. Cloning of AFP Gene and Construction of AFP-expression Plasmids

HepG2 cells were homogenized in RNAzol™B solution, and total RNA was prepared according to the protocol provided with the kit. The cDNA was synthesized by Super-Script™ II Reverse Transcriptase (GIBCO BRL) with an oligo-d(T)$_{12-18}$ primer. AFP gene was amplified from HepG2 cDNA with a gene-specific forward primer: 5'-gcggatccA-CACTGCATAGAAATGAATATG-3' (SEQ ID NO:5), and a gene-specific reverse primer: 5'-gcggatccAACTC-CCAAAGCAGCACGAG-3' (SEQ ID NO:6). The 1.77 kb AFP DNA fragment was cleaved with BamHI and ligated with a BamHI-cleaved pcDNA3 vector. After transformation, plasmids were prepared from an overnight culture of transformed $E.$ $coil$ clones, and further analyzed by restriction enzyme digestion and sequencing. The recombinant plasmid containing AFP gene was named as pcDNA3/AFP.

The 1.77 kb AFP DNA fragment isolated from pcDNA3/AFP by BamHI-cleavage was ligated with a BamHI-cleaved pET32a(+) vector. After transformation, plasmids were prepared from an overnight culture of transformed $E.$ $coli$ clones, and further analyzed by restriction enzyme digestion and sequencing. The recombinant plasmid containing AFP gene was named as pET32a(+)/AFP.

The 1.77 kb AFP DNA fragment isolated from pcDNA3/AFP by BamHI-cleavage was ligated with a BamHI-cleaved pRSET/HspC' vector. After transformation, plasmids were prepared from an overnight culture of transformed $E.$ $coli$ clones, and further analyzed by restriction enzyme digestion and sequencing. The recombinant plasmid containing AFP gene was named as pRSET/AFP-HspC'.

1.3. Cloning of PSA Gene and Construction of PSA-expression Plasmids

Total RNA was prepared from LNCaP cells with RNAzol™B (Tel-Test). LNCaP cDNA was synthesized by SuperScript™ II Reverse Transcriptase (GIBCO BRL) with an oligo-d(T)$_{12-18}$ primer. PSA gene was amplified from LNCaP cDNA with a gene-specific forward primer: 5'-AT-TGTGGGAGGCTGGGAGTG-3' (SEQ ID NO:7) and a gene-specific reverse primer: 5'-GGGGTTGGCCACGATG-GTG-3' (SEQ ID NO:8). The PCR reaction was performed by DyNAzyme™ (FINNZYMES), and the 0.8 kb DNA fragment from PCR reaction was ligated to a pCRII vector (INVITROGEN) directly. After transformation, plasmids were prepared from an overnight culture of transformed $E.$ $coli$ clones, and further analyzed by restriction enzyme digestion and sequencing. The recombinant plasmid containing a sequence encoding the mature PSA was named as pCRII/mPSA.

The 0.8 kb PSA DNA fragment isolated from pCRII/PSA by BamHI/fill-in and XhoI-cleavage was ligated with a BamHI and PvuII-cleaved pRSET/HspC' vector. After transformation, plasmids were prepared from an overnight culture of transformed $E.$ $coli$ clones, and further analyzed by restriction enzyme digestion and sequencing. The recombinant plasmid containing PSA gene was named as pRSET/mPSA-HspC'. The 0.8 kb PSA DNA fragment isolated from pRSET/mPSA-HspC' by BamHI-cleavage was ligated with a BamHI-cleaved pET32a(+) vector. After transformation, plasmids were prepared from an overnight culture of transformed $E.$ $coli$ clones, and further analyzed with restriction enzyme digestion and sequencing. The recombinant plasmid containing PSA gene was named as pET32a(+)/mPSA.

1.4. Expression of Tumor Antigens and Tumor Antigen-HspC' Fusion Proteins

Tumor antigen or tumor antigen-HspC' expression plasmids including pET32a(+)/PSA, pRSET/PSA-HspC', pET32a(+)/AFP and pRSET/AFP-HspC' were used to transform BL21 (DE3) PLysS or BL21 (DE3) RIL (Promega) *E. coli* host strains. Transformed *E. coli* strains were incubated with shaking at 37° C. for overnight. Each culture was inoculated to a fresh AP/LB medium and subsequently incubated with shaking at 37° C. or 3 hours. 0.1 mM of IPTG was added to the medium to induce the expression of the fusion protein. The culture was centrifuged at 8,000×g at 4° C. for 15 minutes to collect the cells. Expression of the pET-tumor antigen or pRSET-tumor antigen-HspC' was examined by comparison of the induced bacterial lysate with the non-induction bacterial lysate, and further confirmed by western blot analysis.

6× His-tagged tumor antigens or 6× His-tagged tumor antigen-HspC' fusion proteins were detected with Ni-NTA-HRP conjugates (QIAGEN). The induced bacterial lysates or fusion proteins were transferred to a Hybond membrane (Amersham Pharmacia) from a polyacrylamide gel after separation according to size by 10% SDS-PAGE, then blocked with TBS buffer (10 mM Tris Cl, pH 7.5, 150 mM NaCl) supplemented with 3% BSA (w/v), and incubated for 1 hour at room temperature in TBS-Tween buffer (20 mM Tris Cl, pH 7.5, 500 mM NaCl, 0.05% (v/v)) containing a 1:1000 dilution of Ni-NTA-HRP conjugate stock solution. After incubation in an ECL detection reagent (Amersham Pharmacia), the membrane was exposed to an X-ray film.

Expression of the HspC' domain in a tumor antigen-HspC' fusion protein was detected with an anti-HspC' monoclonal antibody. The induced-bacterial lysates or fusion proteins were transferred to a Hybond membrane (Amersham Pharmacia) from a polyacrylamide gel after separation according to size by 10% SDS-PAGE, then blocked with TBS buffer (10 mM Tris Cl, pH 7.5, 150 mM NaCl) supplemented with 5% skim milk (w/v), and incubated for 1 hour at room temperature in TBS-Tween buffer (20 mM Tris Cl, pH 7.5, 150 mM NaCl, 0.05% (v/v)) containing anti-HspC' monoclonal antibody. HRP-conjugated goat anti mouse antibody (CHEMICOM cat. AP181P) was used to detect a specific antigen-antibody complex. After incubation in an ECL detection reagent (Amersham Pharmacia), the membrane was exposed to an X-ray film.

Expression of the AFP protein in a tumor antigen and its derivative protein was detected with an anti-AFP monoclonal antibody. The induced-bacterial lysates or fusion proteins were transferred to a Hybond membrane (Amersham Pharmacia) from a polyacrylamide gel after separation according to size by 10% SDS-PAGE, then blocked with TBS supplemented with 5% skim milk (w/v), and incubated for 1 hour at room temperature in TBS-Tween containing mouse anti-human AFP monoclonal antibody (BIOMEDA cat. K004). HRP-conjugated goat anti mouse antibody (CHEMICOM cat. AP181P) was used to detect a specific antigen-antibody complex. After incubation in an ECL detection reagent (Amersham Pharmacia), the membrane was exposed to an X-ray film.

Expression of the PSA protein in a tumor antigen and its derivative protein was detected with an anti-PSA polyclonal antibody. The induced-bacterial lysates or fusion proteins were transferred to a Hybond membrane (Amersham Pharmacia) from a polyacrylamide gel after separation according to size by 10% SDS-PAGE, then blocked with TBS supplemented with 5% skim milk (w/v), and incubated for 1 hour at room temperature in TBS-Tween containing goat anti-human PSA polyclonal antibody (Santa Cruz cat. sc-7638). HRP-conjugated rabbit anti goat antibody (Sigma cat. A5420) was used to detect a specific antigen-antibody complex. After incubation in an ECL detection reagent (Amersham Pharmacia), the membrane was exposed to an X-ray film.

1.5. Purification of Hsp70

*E. coli* strain BL21 (DE3) containing pRSET/Hsp was grown at 37° C. in 1 liter of LB broth containing 50 μg/ml Ampicillin. When absorbance $A_{600}$ reached 0.5–0.6, isopropyl-β-thiogalactoside was added at 1 mM to induce Hsp 70 expression, and the growth was continued for 4 h. Bacterial cells were harvested and stored at −20° C. The cell pellet was suspended in 60 ml of lysis buffer (0.01 M $NaH_2PO_4$, 0.3 M NaCl, pH 8.0) and broken by sonication. The cell lysates were centrifuged at 15,100×g, 4° C. for 15 min, and Hsp70 was solubilized in the supernatant.

A Ni-NTA column (Qiagen) was used to purify Hsp70. The column was equilibrated with 10 column volumes of a wash buffer (0.01 M $NaH_2PO_4$, 0.3 M NaCl, pH 8.0, 20 mM imidazol). After loading, the column was washed with the wash buffer until $A_{280}$ dropped to a baseline. Bound proteins were eluted by a linear gradient containing the wash buffer and imidazol at a concentration of 20–500 mM. The Hsp70 was found in the 44–155 mM imidazol fraction. The pooled fractions were dialysed against PBS and concentrated by a stirring cell (Amicon, YM-10). The purity of the protein was analyzed by SDS-PAGE and the total protein concentration was measured by a BCA protein assay (Pierce).

1.6. Removal of Endotoxin

A polymyxin B agarose column (Pierce, Detoxi-Gel™, 20344) was used to remove endotoxin. The column was regenerated with 5 column volumes of 1% sodium deoxycholate and washed with 5 column volumes of pyrogen-free ddH2O, then equilibrated with 5 column volumes of PBS. The protein was loaded onto the column at 0.4 ml per ml gel volume, then incubated for 1 h at 37° C. The protein was eluted with PBS, concentrated by centrifugation (Centricon, Millipore) and assayed for endotoxin levels.

1.7. Purification of AFP-Hsp and PSA-Hsp

Cell pellets were suspended in 60 ml of lysis buffer (0.01 m $NaH_2PO_4$, 0.3 M NaCl, pH 8.0) and broken by sonication. Inclusion bodies were collected by centrifugation at 15,100× g, 4° C. for 15 min, and treated with a washing buffer (2 M Urea, 5 mM EDTA, 5 mM DTT, 2M Urea, 2% Triton X-100, 100 mM Tris, pH 7.0) followed by centrifugation. The inclusion bodies were resuspended in 10 ml denaturing lysis buffer (6 M guanidine, 0.1 M $NaH_2PO_4$, 0.01 M Tris-HCl, pH 8.0), and mixed for 2 h at room temperature. The guanidine-solubilized protein was purified using Superdex 200. The column was equilibrated with a buffer (50 mM Tris, pH 7.5, 4 M guanidine, 5 mM DTT), and loaded with 4 ml denatured protein sample at a 1 ml/min flow rate. The sample was assayed by SDS-PAGE, and collected in a volume of about 50–60 ml.

1.8. Refolding of Denatured Fusion Proteins

The denatured AFP-Hsp or PSA-Hsp proteins were refolded by rapidly diluting them into a refolding buffer (100 mM Tris, pH 8.0, 0.5 M L-arginine, 10 mM reduced glutathione, 1 mM oxidized glutathione) to a, final protein concentration of about 0.5 mg/ml. The sample was incubated at room temperature for 2 h, and dialyzed against PBS overnight at 4° C. A small amount of insoluble material was removed by centrifugation (15,100×g for 15 min), and the soluble protein was concentrated by ultrafiltration using a YM-10 membrane (Amicon). The purity of the protein was analyzed by SDS-PAGE, and the total protein concentration was measured by a BCA protein assay (Pierce).

1.9. Isolation of Dendritic Cells from Bone Marrow

Femurs and tibiae of 4–12-week old female BALB/c mice were removed and purified from the surrounding muscle tissues by rubbing with Kleenex tissues. Intact bones were left in 70% ethanol for 2–5 min for disinfection and washed with PBS. Then both ends were cut with a pair of scissors, and the marrow was flushed with PBS using a Syringe with a 0.45 μm diameter needle. The clustered bone marrow cells in the suspension were disintegrated by vigorous pipetting. After one wash in PBS, about $1-1.5\times10^7$ leukocytes were obtained per femur or tibia. The method for generating bone marrow-derived dendritic cells (BM-DC) with GM-CSF was adapted from a previous publication (Lutz et al., 1999, J. Immunol. Methods 223, 77–92). Briefly, the isolated bone marrow cells were resuspended to $2-5\times10^5$/ml with RPMI-10:RPMI-1640 (GIBCO BRL, USA) supplemented with penicillin (100 U/ml, Sigma), streptomycin (100 μg/ml, Sigma), L-glutamin (2 mM, Sigma), 2-mercaptoethanol (50 μM, Sigma), and 10% heat-inactivated and filtered (0.22 μm, Millipore) fetal calf serum. At day 0, 10 ml of bone marrow cells were added to Petri-dish containing 200 U/ml (20 ng/ml) recombinant mouse GM-CSF (MoGM-CSH, Peprotech). At day 3, another 10 ml RPMI-10 containing 200 U/ml MoGM-CSF were added to the plates. At day 6 and day 8, half of the culture supernatant was collected, centrifuged, and the cell pellet was resuspended in 10 ml fresh RPMI-10 containing 200 U/ml MoGM-CSF, and delivered back into the original plate. At day 9, dendritic cell qualities were determined by measuring the expression of the surface markers (e.g., CD11c, B7-1, MHC II, and DEC205). Generally, immature dendritic cells were 50% of the total cell population.

1.10. FACS Analysis

Cells ($5-10\times10^5$) were stained with 50 ml fluorescent moeity-conjugated antibodies in PBS containing 1% BSA and 0.1% azide, which also served as a washing buffer. The following antibodies were used for the surface staining: MHC molecule I-A/I-E (2G9, Pharmingen), CD80 (B7-1), CD86 (B7-2), CD11c (N418, Pharmingen), and DEC205 (NLDC-145, Pharmingen).

1.11. Tumor Cell Lines

CT26 is a murine colon carcinoma cell line. CT26/AFP and CT26/PSA were obtained by transfection of CT26 with a cDNA encoding alfa-fetal protein (AFP) or prostate specific antigen (PSA), respectively. These cell lines were maintained in DMEM medium (Life technologies) with 10% FCS, 2 mM L-glutamine, penicillin (100 U/ml, Sigma) and streptomycin (100 μg/ml, Sigma).

1.12. Animal Studies

BALB/c mice received $1\times10^5$ viable CT26/AFP or CT26/PSA tumor cells s.c. in the right flank on day 0. At day 14 after injection, the mice received a local irradiation of 8 Gy. On the following day, 25 μl $5\times10^5$ syngeneic dendritic cells or PBS were injected into the tumor area. In some groups, dendritic cells were mixed with HSPs or Hsp fusion proteins (50 μg) before injection. The size of the tumor was measured at least three times weekly and recorded as length (L) and width (W). The tumor volumes were calculated as $L\times W^2/2$. Tumor volume ratio was determined by comparing to the tumor volume at day 14, which was defined as 1.

1.13. Cytotoxicity Assay

At day 35 after tumor injection, mice were killed and the spleen was harvested. Erythrocyte-depleted splenocytes ($1\times10^6$ cells/ml) were cultured in vitro with mytomycin C-treated CT26/PSA tumor cells ($1\times10^6$ cells/ml) in 24-well plates for 5 days. On each day, recombinant human IL-2 was added at 50 U/ml. On day 5, all cells were collected, and dead cells were removed by density gradient. The resulting viable cells were then tested for specific cytotoxicity in a standard 5-h 51 Cr-release assay. Specific cytotoxicity percentage was calculated as 100×[(experimental release—spontaneous release)/(maximal release—spontaneous release)].

1.14. Analysis of Phagocytosis

CT26/PSA tumor cells were stained with green dye PKH-67 (Sigma) according to the manufacturer's describedprotocol. Briefly, tumor cells were suspended to $1\times10^7$/ml and PKH-67 (2 mg/ml) was added dropwise. After incubation at 37° C. for 10 min, cells were washed three times with PBS. For induction of apoptosis, tumor cells ($2\times10^6$) were seeded in a T25 tissue culture flask and 24 h later exposed to 100 cGy of irradiation. DThe dendritic cells were cocultured with apoptotic cells at 37° C. for 24 h at 1:1 ratio. The cells were harvested, and the dendritic cells were stained with a PE-labeled anti-CD86 antibody. Two-color flow cytometry was performed to determine the percentage of cells that phagocytosed apoptotic cells.

1.15. Apoptosis Detection by TUNEL Assay

Apoptosis was measured with a terminal deoxynucleotidyl transferase-mediated dUTP-biotin nick end labeling (TUNEL) assay. The TUNEL assay was performed by using commercial TdT-FragEL™ DNA fragmentation detection kit (Cat. No. QIA33, Oncogen). Briefly, tumors were cut from mice and paraffin sections were made. After hydration and dehydration, the slides were fixed with 4% paraformaldehyde in PBS and permeabilized with 20 μg/ml proteinase K in 10 mM Tris, pH 8 for 10 minutes at room temperature. Then the endogenous peroxidases were inactivated by 3% $H_2O_2$ in methanol for 5 minutes at room temperature. After washing, cells were incubated with biotin-labeled dNTP in the presence of terminal deoxynucleotidyl transferase enzyme solution for 1.5 h at 37° C. After incubation, biotinylated nucleotides were detected with a streptavidin-horseradish peroxidase conjugate for 25 minutes at room temperature. Diaminobenzidine reacted with the labeled sample for 15 minutes at room temperature. Finally, tumor cells were counterstained with methyl green for 3 minutes at room temperature.

2. Protein Expression and Purification

Alpha-fetoprotein (AFP) gene was synthesized from human placental tissue with RT-PCR and subcloned to an E. coli-expression plasmid. A full-length AFP protein fused with a N-terminal pET tag domain consisting of 6× His-, thioredoxin- or S-tags was expressed in E. coli transformed with plasmid pET32a(+)/AFP. The recombinant protein was verified with a Ni-NTA-HRP conjugate and an anti-AFP antibody by Western blot analysis. A full-length AFP protein fused with a N-terminal 6× His-tag domain and a C-terminal HspC' domain containing amino acids 480–640 of HspC' protein was expressed in E. coli. transformed with plasmid pRSET/AFP-HspC'. The recombinant protein was verified with a Ni-NTA-HRP conjugate, an anti-AFP antibody and an anti-HspC' antibody by Western blot analysis.

Prostate specific antigen (PSA) gene was synthesized from human LNCaP cell line with RT-PCR and subcloned to an *E. coli*-expression plasmid. A mature form of PSA protein fused with a N-terminal pET tag domain consisting of 6× His-, thioredoxin- or S-tags was expressed in *E. coli* transformed with plasmid pET32a(+)/mPSA. The recombinant protein was verified with a Ni-NTA-HRP conjugate and an anti-PSA antibody by Western blot analysis. A mature form of PSA protein fused with a N-terminal 6× His-tag domain and a C-terminal HspC' domain containing amino acids 480–640 of Hsp70 protein was expressed in *E. coli* transformed with plasmid pRSET/mPSA-HspC'. The recombinant protein was verified with a Ni-NTA-HRP conjugate, an anti-PSA antibody and an anti-HspC' antibody by Western blot analysis. Hsp 70 protein was prepared from the soluble fraction after cell breakage and was loaded onto a Ni-NTA column, and eluted with a linear gradient of imidazole from 20 mM to 500 mM. Hsp 70 was eluted at 100 mM imidazole. The purity of the protein was more than 90% as determined by Coomassie Blue staining. HSP fusion proteins PSA-HspC' and AFP-HspC' were purified by a Ni-column under denatured conditions. Pooled fractions were refolded as described in Section 1.8. Endotoxin contamination was removed by polymyxin B affinity column. The endotoxin levels in purified proteins were measured by the LAL (Limulus amebocyte lysate, Cape Cod Inc.) method, and were found less than 2.5 U/μg in all proteins.

3. Generation of BM-DC

Our protocol to generate BM-DC was adapted from the method of Lutz et al. as described in section 1.9. This protocol routinely generated 1–3×10$^8$ immature and mature dendritic cells per mouse at 90–95% purity. BM-DC were characterized by measuring MHC II and costimulatory molecules (e.g., CD40, CD80, and CD86) expression. Dendritic cell surface markers were analyzed by flow cytometry at days 7, 8, 9, 10, and 12. The suspension population was subdivided into smaller immature and mature BM-DC groups on the basis of their DEC-205 molecules. Immature dendritic cells have higher yield at day 9, which was about 50% of the population.

4. Phagocytosis of Dead Tumor Cells by BM-DC

In order to test phagocytosis ability of BM-DC, CT26 cells were labeled with a fluorescent green dye (PKH-67), and BM-DC were then stained with CD86-PE. The heat-induced necrosis (50° C., 30 min) (Rubartelli et al., 1997, Eur. J. Immunol. 27, 1893–1900), and irradiation-induced apoptotic CT26 tumor cells were coincubated with BM-DC. After 16–20 h, the cocultured cells were analyzed by FACSCalibur, allowing quantification of phagocytosis. Low temperature (i.e., 4° C. for 16 hrs inhibited uptake of CT26 by BM-DC. When BM-DC were mixed with labeled CT26 cells and incubated at 37° C. for 16 hrs, thirty percent of the irradiated cells were phagocytosed by BM-DC. These unexpected results demonstrate that immature dendritic cells can be isolated from BM and retain their phagocytosis ability of uptaking dead tumor cells.

5. Apoptosis Detection by TUNEL Assay

To obtain evidence for apoptosis after irradiation, tumor mass was cut from mice and paraffin-embedded sections were generated. The slides were deparaffined and subject to a TUNEL assay which measures DNA fragmentation.

6. Anti-tumor Immunity Induced by BM-DC and HSP or HSP Fusion Protein

To determine therapeutic effects of HSPs or HSP fusion proteins in dendritic cell-based immunotherapy after tumor irradiation, mice were injected with dendritic cells and proteins in the tumor regions. Unexpectedly, mice treated with BM-DC and proteins showed that tumor growth was inhibited in the HSP and PSA-Hsp groups. In addition, the therapeutic effect of heat shock proteins was demonstrated not only in the CT26/PSA model, but also in the CT26/AFP animal model. The anti-tumor effect of the treatment indicates that heat shock proteins play an important role in the immune response. Mice that had survived were rechallenged with parental tumor cells, and the growth of tumor cells was inhibited in heat shock protein-treated groups. As shown in Table 1 below, mice lived more than 50 days after vaccination with BM-DC mixed with HSPs or PSA-Hsp. Mice that had survived more than 50 days were rechallenged with CT26/PSA at 1×10$^5$ cells/mouse s.c. in the left flank. Tumor growth was measured three times a week. Mice with tumor volume growing more than 2.5 cm$^3$ were defined as dead. The long-term systemic immunity was elicited by local administration of dendritic cells and heat shock proteins.

TABLE 1

| Groups | Survival (%) | Rechallenge survival (%) |
|---|---|---|
| Control | 0/10 | |
| RT only | 2/10 | |
| RT/DC | 3/10 | |
| RT/DC/Hsp | 6/10 | 3/6 (50%) |
| RT/DC/PSA-Hsp | 8/10 | 7/8 (87%) |

Control: no treatment;
RT only: irradiation only;
RT/DC: irradiation combined with BM-DC;
RT/DC/Hsp: irradiation combined with BM-DC and Hsps;
RT/DC/PSA-Hsp: irradiation combined with BM-DC and PSA-HspC'.

7. Cytotoxicity Assay

To examine the anti-tumor mechanisms of the therapy, we performed a cytotoxicity assay. Spenocytes from treated mice were cocultured with mytomycin-C treated CT26/PSA cells. After 5 days in culture, spenocytes were used as effector cells in a chromium release assay. Unexpectedly, spenocytes derived from mice treated with BM-DC and heat shock proteins displayed enhanced cytotoxicity to CT26/PSA cells than those mice treated with dendritic cells only. Our data indicate that injection of BM-DC mixed with heat shock proteins is able to induce more efficient cytotoxic T-cell responses against CT26/PSA than BM-DC injection without heat shock proteins.

Other Embodiments

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the scope of the following claims.

What is claimed is:

1. An immunogenic composition comprising
   (i) antigen-presenting cells;
   (ii) a purified fragment of human Hsp 70, consisting essentially of amino acids 480–640 of the human Hsp 70, fused to a human antigen unrelated to a heat shock protein; and
   (iii) a pharmaceutically acceptable carrier,
wherein the composition is free of any human antigen that is not covalently bound to the fragment of human Hsp 70.

2. The immunogenic composition of claim 1, wherein the antigen-presenting cells include dendritic cells.

3. The immunogenic composition of claim 2, wherein the antigen-presenting cells are purified.

4. The immunogenic composition of claim 3, wherein the human antigen is alpha-fetal protein or prostate specific antigen.

5. The immunogenic composition of claim 1, wherein the antigen-presenting cells are purified.

6. The immunogenic composition of claim 1, wherein the human antigen is a tumor associated antigen.

7. The immunogenic composition of claim 1, further comprising a cytotoxic compound.

8. The immunogenic composition of claim 7, wherein the antigen-presenting cells include dendritic cells.

9. The immunogenic composition of claim 7, wherein the antigen-presenting cells are purified.

10. The immunogenic composition of claim 7, wherein the human antigen is a tumor associated antigen.

11. The immunogenic composition of claim 1, wherein the human antigen is a prostate specific antigen.

12. The immunogenic composition of claim 1, wherein the human antigen is an alpha-fetal protein.

* * * * *